United States Patent
Guarna et al.

(10) Patent No.: US 6,723,850 B1
(45) Date of Patent: Apr. 20, 2004

(54) PROCESS FOR THE SYNTHESIS OF (1-H)-BENZO[C]QUINOLIZIN-3-ONES DERIVATIVES

(75) Inventors: Antonio Guarna, Seano-Carmigiano (IT); Mario Serio, Bagno a Ripoli (IT); Ernesto Occhiato, Florence (IT)

(73) Assignee: Applied Research Systems ARS Holding N.V., Curacao (AN)

( * ) Notice: Subject to any disclaimer, the term of this patent is extended or adjusted under 35 U.S.C. 154(b) by 0 days.

(21) Appl. No.: 09/743,373

(22) PCT Filed: Jul. 23, 1999

(86) PCT No.: PCT/EP99/05277

§ 371 (c)(1),
(2), (4) Date: May 25, 2001

(87) PCT Pub. No.: WO00/08019

PCT Pub. Date: Feb. 17, 2000

(30) Foreign Application Priority Data

Aug. 3, 1998 (EP) .............................. 98114524

(51) Int. Cl.⁷ .............................................. C07D 445/06
(52) U.S. Cl. ....................................................... 546/95
(58) Field of Search .................... 546/108, 95; 514/294

(56) References Cited

FOREIGN PATENT DOCUMENTS

| WO | WO 97 29107 | | 8/1997 |
|----|-------------|---|--------|
| WO | 9729107 | * | 8/1997 |

OTHER PUBLICATIONS

Buzas; J. Heterocyclic Chem. 11(2): 175–6, 1974.
Oare; J. Organic Chem. 55(1):132–57, 1990.
Barrett; J. Chem. Soc. 1964:788–92.
Fang; Tetrahedron Lett. 30(28):3625–8, 1989.
Buzas; J. Heterocyclic Chem. 11(2): 175–6, 1974.
Oare; J. Organic Chem. 55(1):132–57, 1990.
Barrett; J. Chem. Soc. 1964:788–92.
Fang; Tetrahedron Lett. 30(28):3625–8, 1989.
Takahata; Heterocycles 24(1):37–39 (1986).

* cited by examiner

*Primary Examiner*—Alan L. Rotman
*Assistant Examiner*—Binta Robinson
(74) *Attorney, Agent, or Firm*—Hedman & Costigan, P.C.

(57) ABSTRACT

The present invention refers to a process for the preparation of (1H)-benzo[c]quinolizin-3-ones derivatives of general formula (I) which involves only three steps and the use, as starting products, of commercially available, or easily preparable, compounds. The compounds of formula (I) are useful as inhibitors of 5α-reductases.

3 Claims, No Drawings

PROCESS FOR THE SYNTHESIS OF (1-H)-BENZO[C]QUINOLIZIN-3-ONES DERIVATIVES

SUMMARY OF THE INVENTION

The present invention refers to a process for the preparation of (1H)-benzo[c]quinolizin-3-ones derivatives of general formula (I) which involves only three steps and the use, as starting products, of commercially available, or easily preparable, compounds. The compounds of formula (I) are useful as inhibitors of 5α-reductases.

FIELD OF THE INVENTION

The present invention refers to a process for the preparation of (1H)-benzo[c]quinolizin-3-ones derivatives of general formula (I)
wherein:

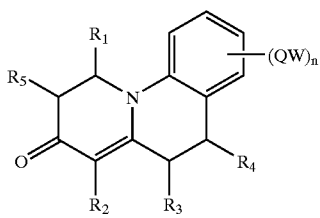

I $R_1$, $R_2$, $R_3$, $R_4$, $R_5$, same or different, are chosen in the group consisting of: H, $C_{1-8}$alkyl, $C_{2-8}$alkenyl, $C_{2-8}$alkinyl, cycloalkyl, aryl, heterocycle, halogen, CN, azide, NRR', $C_{1-8}$alkylamino, arylamino, $C_{1-8}$alkyloxy, aryloxy, COOR, CONRR' wherein R and R', same or different, are chosen in the group consisting of: H, $C_{1-8}$alkyl, cycloalkyl, aryl, heterocycle, aryl$C_{1-8}$alkyl;

Q is chosen in the group consisting of: simple bond, $C_{1-8}$alkyl, $C_{2-8}$alkenyl, $C_{2-8}$alkinyl, cycloalkyl, CO, CONR, NR, wherein R is as above defined;

W is chosen in the group consisting of: H, $C_{1-8}$alkyl, $C_{2-8}$alkenyl, $C_{2-8}$alkinyl, cycloalkyl, trifluoromethyl, $C_{1-8}$alkoxy, $C_{1-8}$alkoxy-$C_{1-8}$alkyl, aryl$C_{1-8}$alkyl, aryl, aryloxy, arylamino, $C_{1-8}$alkylcarbonyl, arylcarbonyl, arylcarboxyl, arylcarboxyamide, halogen, CN, NRR', $C_{1-8}$alkylamino, heterocycle wherein the groups alkyl, alkenyl, alkinyl, cycloalkyl, aryl, heterocycle, can be substituted;

n is an integer comprised between 1 and 4;
and their pharmaceutically acceptable salts or esters, starting from commercially available, or easily preparable compounds, and involving only three steps.

STATE OF THE ART

Compounds of general formula (I) as above defined are known 5α-reductases inhibitors useful for the treatment of the pathologies mediated by the enzyme (for example acne, baldness, prostatic cancer and hypertrophy in men and hirsutism in women) (see International Application No PCT/EP97/00552). They are also active as plant growth regulators.

As it is described in the above said patent application, up to now the compounds of formula (I) are produced by a process involving various steps starting from a compound of formula II

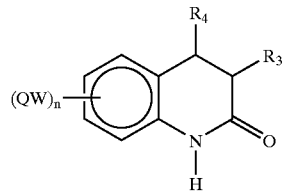

According to the process the amide-group of compound II is protected as N-Boc derivative, the obtained compound is reduced, reacted with a silyloxydiene produced "in situ" and hydrolized to obtain a compound of formula III

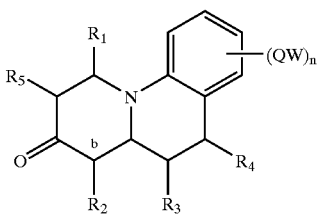

Finally the introduction of the double bond in position b is performed by reaction with dichlorodicyanoquinone with the corresponding silylenolethers or by oxidation with mercuric acetate.

As it can be seen the above described process involves many steps which i.a. have a negative effect on the final yields of the desired compounds.

In view of the importance of these compounds as 5α-reductase inhibitors, it is evident the interest in making available new processes in order to prepare the desired compounds in a more efficient way.

DETAILED DESCRIPTION OF THE INVENTION

The present invention allows to overcome the above said problems by a synthesis process that involves only three steps and moreover uses, as starting compounds, compounds which can be easily synthesized or are commercially available.

According to the present invention in the compounds of formula (I) group $C_{1-8}$alkyl, $C_{2-8}$alkenyl and $C_{2-8}$alkinyl represent linear or branched alkyl radicals as for example: methyl, ethyl, propyl, isopropyl, butyl, pentyl, hexyl, heptyl, octyl, ethylene, propene, butene, isobutene, acetylene, propine, butine ecc.

The term cycloalkyl represents: cyclopropane, cyclobutane, cyclopentane, cyclohexane, cycloheptane, cyclooctane, norbornane, canphane, adamantane.

The term aryl represents: phenyl and naphtyl.

The term heterocycle represents in particular: saturated or aromatic heterocycles containing one or more N atoms, more particularly: pyridine, imidazole, pyrrole, indole, triazoles, pyrrolidine, pyperidine.

Halogen means: fluorine, chlorine, bromine, iodine.

The substituents of the above said group W are preferably: halogen, OR, phenyl, NRR', CN, COOR, CONRR', $C_{1-8}$alkyl (wherein R and R' are as above defined).

In particular, the process according to the present invention allows the preparation of the compounds of formula (I) wherein:

Q=simple bond, CO, CONR, NR (wherein R is as above defined) W=H, F, Cl, Br, Me, t-butyl, $C_{1-8}$alkoxy, 2,5-dimethylhexyl, trifluoromethyl, 2,5-(ditrifuoromethyl)phenyl, 4-methoxy-phenyl, 4-fluorophenyl, phenyl, phenyl-$C_{1-8}$alkyl, $C_{1-8}$alkylcarbonyl, phenylcarbonyl.

n=1 or 2

$R_1$, $R_2$, $R_3$, $R_4$, $R_5$=H, Me, CN, phenyl, COOR, CONRR' (wherein R and R' are as above defined).

Among the pharmaceutically acceptable esters and salts according to the present invention the following can be mentioned: hydrochloride, sulphate, citrate, formiate, phosphate.

Specific compounds prepared according to the process of the invention are:

2,3,5,6-tetrahydro-(1H)-benzo[c]quinolizin-3-one;

8-chloro-2,3,5,6-tetrahydro-(1H)-benzo[c]quinolizin-3-one;

2,3,5,6-tetrahydro-8-methyl-(1H)-benzo[c]quinolizin-3-one;

2,3,5,6-tetrahydro-4-methyl-(1H)-benzo[c]quinolizin-3-one;

2,3,5,6-tetrahydro-1-methyl-(1H)-benzo[c]quinolizin-3-one;

8-chloro-2,3,5,6-tetrahydro-4-methyl-(1H)-benzo[c]quinolizin-3-one;

2,3,5,6-tetrahydro-4,8-dimethyl-(1H)-benzo[c]quinolizin-3-one;

8-chloro-2,3,5,6-tetrahydro-1-methyl-(1H)-benzo[c]quinolizin-3-one;

2,3,5,6-tetrahydro-1,4-dimethyl-(1H)-benzo[c]quinolizin-3-one;

2,3,5,6-tetrahydro-6-methyl-(1H)-benzo[c]quinolizin-3-one;

8-chloro-2,3,5,6-tetrahydro-6-methyl-(1H)-benzo[c]quinolizin-3-one;

2,3,5,6-tetrahydro-6,8-dimethyl-(1H)-benzo[c]quinolizin-3-one;

2,3,5,6-tetrahydro-4,6-dimethyl-(1H)-benzo[c]quinolizin-3-one;

2,3,5,6-tetrahydro-1,6-dimethyl-(1H)-benzo[c]quinolizin-3-one;

8-chloro-2,3,5,6-tetrahydro-4,6-dimethyl-(1H)-benzo[c]quinolizin-3-one;

2,3,5,6-tetrahydro-4,6,8-trimethyl-(1H)-benzo[c]quinolizin-3-one;

8-chloro-2,3,5,6-tetrahydro-1,6-dimethyl-(1H)-benzo[c]quinolizin-3-one;

2,3,5,6-tetrahydro-1,4,6-trimethyl-(1H)-benzo[c]quinolizin-3-one;

2,3,5,6-tetrahydro-5-methyl-(1H)-benzo[c]quinolizin-3-one;

8-chloro-2,3,5,6-tetrahydro-5-methyl-(1H)-benzo[c]quinolizin-3-one;

2,3,5,6-tetrahydro-5,8-dimethyl-(1H)-benzo[c]quinolizin-3-one;

2,3,5,6-tetrahydro-4,5-dimethyl-(1H)-benzo[c]quinolizin-3-one;

2,3,5,6-tetrahydro-1,5-dimethyl-(1H)-benzo[c]quinolizin-3-one;

8-chloro-2,3,5,6-tetrahydro-4,5-dimethyl-(1H)-benzo[c]quinolizin-3-one;

2,3,5,6-tetrahydro-4,5,8-trimethyl-(1H)-benzo[c]quinolizin-3-one;

8-chloro-2,3,5,6-tetrahydro-1,5-dimethyl-(1H)-benzo[c]quinolizin-3-one;

2,3,5,6-tetrahydro-1,4,5-trimethyl-(1H)-benzo[c]quinolizin-3-one;

2,3,5,6-tetrahydro-5,6-dimethyl-(1H)-benzo[c]quinolizin-3-one;

8-chloro-2,3,5,6-tetrahydro-5,6-dimethyl-(1H)-benzo[c]quinolizin-3-one;

2,3,5,6-tetrahydro-5,6,8-trimethyl-(1H)-benzo[c]quinolizin-3-one;

2,3,5,6-tetrahydro-4,5,6-trimethyl-(1H)-benzo[c]quinolizin-3-one;

8-chloro-2,3,5,6-tetrahydro-4,5,6-trimethyl-(1H)-benzo[c]quinolizin-3-one;

2,3,5,6-tetrahydro-1,5,6-trimethyl-(1H)-benzo[c]quinolizin-3-one;

8-chloro-2,3,5,6-tetrahydro-1,5,6-trimethyl-(1H)-benzo[c]quinolizin-3-one;

2,3,5,6-tetrahydro-4,5,6,8-tetramethyl-(1H)-benzo[c]quinolizin-3-one.

According to the invention the above defined compounds of formula (I) can be prepared starting from compounds of general formula 2 and 3:

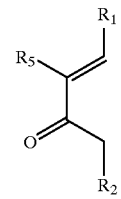

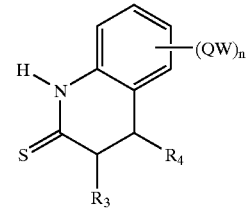

wherein $R_1$, $R_2$, $R_3$, $R_4$, $R_5$, W, Q and n are as above defined.

The compounds 2 and 3 are commercially available or can be prepared according to known techniques.

As it can be seen from the Scheme 1 the preparation of the compounds I according to the invention involves the N-alkylation of the thioamide 3 with the vinyl ketone 2 to give the N-alkylated thioamide 4 in the presence of a strong, but not nucleophilic, base. Preferably the reaction is performed in an organic solvent (for example THF) at a temperature comprised between 0° C.–30° C. for a time comprised between two and four hours. More preferably the vinyl ketone is added to the thioamide intermittently.

The characteristics of the base are crucial for the effectiveness of the reaction: indeed strong nucleophilic bases cause the polymerization of the vinylketone, whereas with mild bases the reaction does not occur. Preferred bases having the above said characteristics are: $K_2CO_3$/18-crown-6 or diazabicycloundecene (DBU). The N-alkylated thioamide 4 is then methylated at sulfur atom, to give the salt 5, which is not usually isolated, but left to react with a base to give the final compound 1. Also for this step the reaction conditions (temperature and time) and the type of base are important.

The best results were obtained using dimethyl sulfate as methylating agent, a strong but not nucleophilic base (for example DBU) and performing the reaction at refluxing temperature in an organic solvent (for example toluene) for a time comprised between half–and one hour.

The synthesis of two compounds of formula (I) is reported in the following examples in order to better illustrate the invention.

EXAMPLE 1

Preparation of 6-Chloro-1-(3-oxo-1-pentyl)-(1H)-3, 4-dihydroquinolin-2-thione [Compound 4 Wherein $(QW)_n$=Cl, $R_1$=$R_3$=$R_4$=$R_5$=H, $R_2$=Me]

Under nitrogen atmosphere, ethyl vinyl ketone (compound 2, wherein $R_1$=$R_5$=H, $R_2$=Me) (340 ml, 3.42 mmol) is added to a stirred suspension of 6-chloro-(1H)-3, 4-dihydroquinolin-2-thione (compound 3 wherein $(QW)_n$= Cl, $R_3$=$R_4$=H) (450 mg, 2.28 mmoli), anhydrous $K_2CO_3$ (692 mg, 5.01 mmol), and 18-crown-6 (60 mg, 0.23 mmol) in anhydrous THF (41 ml), while cooling at 0° C. The suspension is then allowed to warm to room temperature and, after 30 min of stirring, the suspension is cooled at 0° C. and a further amount of ethyl vinyl ketone (3.42 mmol) is added. After 1 h at room temperature the suspension is cooled again at 0° C. and the last amount of ethyl vinyl ketone (3.42 mmol) is added. After 1 h at room temperature the reaction is thus complete. The reaction mixture is filtered through a short pad of anhydrous $Na_2SO_4$ and the solvent evaporated. The residual oil is chromatographed (ethyl acetate: light petroleum ether, 1:9, $R_f$=0.29) affording pure 6-chloro-1-(3-oxo-1-pentyl)-(1H)-3,4-dihydroquinolin-2-thione [compound 4 wherein $(QW)_n$=Cl, $R_1$=$R_3$=$R_4$=$R_5$=H, $R_2$=Me] (277 mg, 45%) as a pale yellow solid (mp. 68–70° C.).

As an alterative, thioamide 3 (450 mg, 2.28 mmol) is dissolved in 5 ml of anhydrous THF, DBU (69 ml, 0.46 mmol) is added and, while cooling at 0° C., ethylvinylketone 2 (275 ml, 2.76 mmol) is added dropwise under stirring and nitrogen atmosphere. After 2.5 h at 0° C. a further amount of ethyl vinyl ketone (113 ml, 1.38 mmol) is added, the reaction is left another hour at 0° C. and then the solvent is evaporated, the residual oil diluted with $CH_2Cl_2$ (30 ml), washed with 5% citric acid, $NaHCO_3$ (satd) and water. The organic layer is dried over $Na_2SO_4$, filtered and evaporated, obtaining a crude oil which is chromatographed as reported above. Compound 4 is thus obtained as a 1.6:1 mixture with unreacted thioamide 3. Calculated yield on 4: 35%.

EXAMPLE 2

Preparation of 8-Chloro-2,3,5,6-tetrahydro-4-methyl-(1H)-benzo[c]quinolizin-3-one [Compound I Wherein $(QW)_n$=Cl, $R_1$=$R_3$=$R_4$=$R_5$=H and $R_2$=Me]

To a solution of 6-chloro-1-(3-oxo-1-pentyl)-(1H)-3,4-dihydroquinolin-2-thione [compound 4 wherein $(QW)_n$=Cl, $R_1$=$R_3$=$R_4$=$R_5$=H, $R_2$=Me], (250 mg, 0.93 mmol) in anhydrous toluene (3 ml) is added $Me_2SO_4$ (149 ml, 1.57 mmol) under stirring and nitrogen atmosphere. The solution is heated at reflux and after 5 min a red oil begins to separate. After further 10 min, DBU (235 ml, 1.57 mmol) is added dropwise to the refluxing two-phase reaction mixture, causing after a few minutes, a darkening of the mixture. The reflux is maintained for 20 min, then the solution is cooled at room temperature, diluted with dichloromethane (50 ml), washed with water (50 ml) and dried over $Na_2SO_4$. After filtration and evaporation of the solvent the dark residual oil is chromatographed (ethyl acetate: light petroleum ether, 1:1, $R_f$=0.28) affording pure 8-chloro-2,3,5,6-tetrahydro-4-methyl-(1H)-benzo[c]quinolizin-3-one [compound 1 wherein $(QW)_n$=Cl, $R_1$=$R_3$=$R_4$=$R_5$=H and $R_2$=Me] (90 mg, 41%) as an oil which solidify on standing (mp 112–114° C.).

EXAMPLE 3

Preparation of 6-Methyl-1-(3-oxo-1-pentyl)-(1H)-3, 4-dihydroquinolin-2-thione [Compound 4 Wherein $(QW)_n$=Me, $R_1$=$R_3$=$R_4$=$R_5$=H, $R_2$=Me]

Under nitrogen atmosphere, ethyl vinyl ketone (compound 2, wherein $R_1$=$R_5$=H, $R_2$=Me) (380 ml, 3.81 mmol) is added to a stirred suspension of 6-methyl-(1H)-3, 4-dihydroquinolin-2-thione (compound 3 wherein $(QW)_n$= Me, $R_3$=$R_4$=H) (500 mg, 2.82 mmoli), anhydrous $K_2CO_3$ (900 mg, 6.5 mmol), and 18-crown-6 (89 mg, 0.28 mmol) in anhydrous THF (47 ml), while cooling at 0° C. The suspension is then allowed to warm to room temperature and, after 60 min of stirring, the suspension is cooled again at 0° C. and a further amount of ethyl vinyl ketone 2 (3.81 mmol) is added. After 2 h at room temperature the reaction is complete. The reaction mixture is filtered through a short pad of anhydrous $Na_2SO_4$ and the solvent evaporated. The residual oil is chromatographed (ethyl acetate:light petroleum ether, 1:9, $R_f$=0.23) affording pure 6-methyl-1-(3-oxo-1-pentyl)-(1H)-3,4-dihydroquinolin-2-thione [compound 4 wherein $(QW)_n$=Me, $R_1$=$R_3$=$R_4$=$R_5$=H, $R_2$=Me] (500 mg, 68%) as a white solid (mp 70–71° C.).

EXAMPLE 4

Preparation of 8-Methyl-2,3,5,6-tetrahydro-4-methyl-(1H)-benzo[c]quinolizin-3-one [Compound I Wherein $(QW)_n$=Me, $R_1$=$R_3$=$R_4$=$R_5$=H and $R_2$=Me]

To a solution of 6-methyl-1-(3-oxo-1-pentyl)-(1H)-3,4-dihydroquinolin-2-thione [compound 4 wherein $(QW)_n$=Me, $R_1$=$R_3$=$R_4$=$R_5$=H, $R_2$=Me] (350 mg, 1.40 mmol) in anhydrous toluene (4 ml) is added $Me_2SO_4$ (227 ml, 2.40 mmol) under stirring and nitrogen atmosphere. The solution is heated at reflux and after 5 min a red oil begins to separate. After further 15 min, DBU (365 ml, 2.40 mmol) is added dropwise to the refluxing two-phase reaction mixture, causing after a few minutes, a darkening of the mixture. The reflux is maintained for 20 min, then the solution is cooled at room temperature, diluted with dichloromethane (50 ml), washed with water (50 ml) and dried over $Na_2SO_4$. After filtration and evaporation of the solvent, the dark residual oil is chromatographed (ethyl acetate:light petroleum ether, 1:1, $R_f$=0.29) affording pure 8-methyl-2,3,5,6-tetrahydro-4-methyl-(1H)-benzo[c]quinolizin-3-one [compound I wherein $(QW)_n$=Me, $R_1$=$R_3$=$R_4$=$R_5$=H and $R_2$=Me] (152 mg, 50%) as an oil which became a solid on standing (mp 143–145° C.)

SCHEME 1

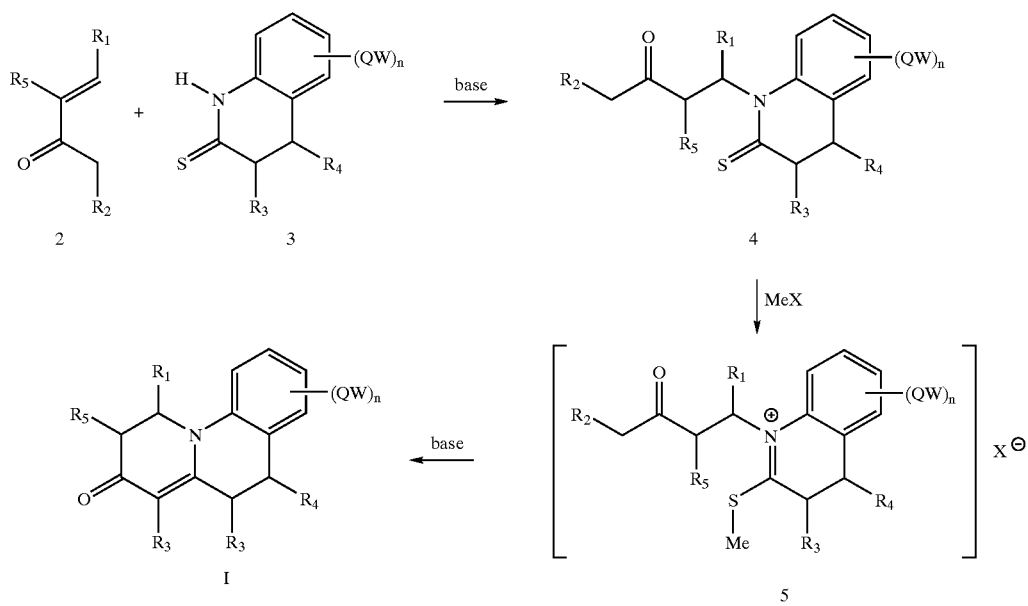

What is claimed is:
1. Process for the preparation of compounds of formula (I):

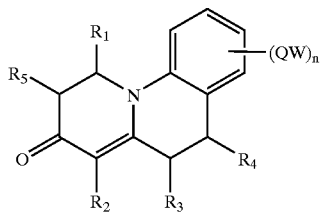

wherein:
R$_1$, R$_2$, R$_3$, R$_4$, R$_5$, are the same or different, are chosen from the group consisting of H, C$_{1-8}$alkyl, C$_{2-8}$ alkenyl, C$_{2-8}$alkinyl, cycloalkyl, aryl, halogen, CN, azide, NRR', C$_{1-8}$alkylamino, arylamino, C$_{1-8}$alkyloxy, arylyoxy, COOR, CONRR' wherein R and R' are the same or different, are chosen from the group consisting of H, C$_{1-8}$ alkyl, cyclopropane, cyclobutane, cyclopentane, cyclohexane, cycloheptane, cyclooctane, phenyl, naphthyl, arylC$_{1-8}$alkyl;

Q is selected from the group consisting of a single bond, C$_{1-8}$alkyl, C$_{2-8}$alkenyl, C$_{2-8}$alkinyl, cycloalkyl, CO, CONR, NR, wherein R is as above defined;

W is selected from the group consisting of H, C$_{1-8}$alkyl, C$_{2-8}$alkenyl, C$_{2-8}$alkinyl, cyclopropane, cyclobutane, cyclopentane, cyclohexane, cycloheptane, trifluoromethyl, C$_{1-8}$ alkoxy, C$_{1-8}$ alkoxy-C$_{1-8}$alkyl, arylC$_{1-8}$alkyl, aryl, aryloxy, arylamino, C$_{1-8}$alkylcarbonyl, arylcarbonyl, arylcarboxyl, arycarboxyamide, halogen, CN, NRR', C$_{1-8}$alkylamino, wherein the groups alkyl, alkenyl, alkinyl, cycloalkyl, naphthyl, phenyl, can be substituted by halogen OR, phenyl, NRR', CN, COOR, CONRR', C$_{1-8}$alkyl, wherein R and R' are as above defined;

n is an integer between 1 and 4;

wherein:
a thioamide of formula 3:

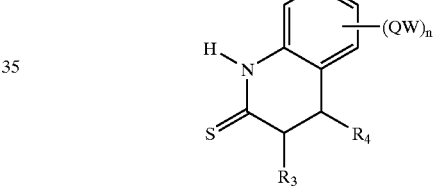

wherein R$_3$ and R$_4$ are as above defined is N-alkylated with a vinyl ketone of formula 2:

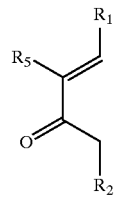

wherein R$_1$, R$_2$ and R$_3$ are as above define to give the corresponding compound 4:

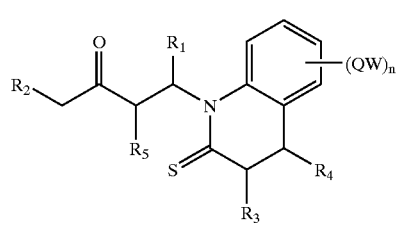

wherein all of the substituents are as above defined said compound being methylated, at the sulfur atom to give the salt 5:

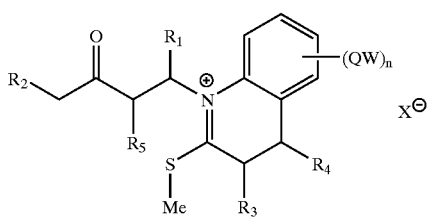

wherein all the substituents are as above defined said compound 5 being directly reacted with a base to give compound 1.

2. Process for the preparation of compound of formula (I):

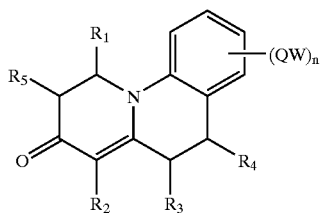

wherein:

R$_1$, R$_2$, R$_3$, R$_4$, R$_5$, are the same or different, and are selected from the group consisting of H, C$_{1-8}$ alkyl, C$_{2-8}$ alkenyl, C$_{2-8}$alkinyl, cyclopropane, cyclobutane, cyclopentane, cyclohexane, cycloheptane, phenyl, naphthyl, halogen, C, azide, NRR', C$_{1-8}$alkylamino, arylamino, C$_{1-8}$alkyloxy, arylyoxy, COOR, CONRR' wherein R and R' are the same or different, are selected from the group consisting of H, C$_{1-8}$ alkyl, cyclopropane, cyclobutane, cyclopentane, cyclohexane, cycloheptane, phenyl, naphthyl, arylC$_{1-8}$alkyl;

Q is chosen in the group consisting of a single bond, C$_{1-8}$alkyl, C$_{2-8}$alkenyl, C$_{2-8}$alkinyl, cycloalkyl, CO, CONR and NR, wherein R is as above defined;

W is selected from the group consisting of H, C$_{1-8}$alkyl, C$_{2-8}$alkenyl, C$_{2-8}$alkinyl, cyclopropane, cyclobutane, cyclopentane, cyclohexane, cycloheptane, trifluoromethyl, C$_{1-8}$ alkoxy, C$_{1-8}$, alkoxy-C$_{1-8}$alkyl, arylC$_{1-8}$alkyl, phenyl, naphthyl, aryloxy, arylamino, C$_{1-8}$alkylcarbonyl, arylcarbonyl, arylcarboxyl, arycarboxyamide, halogen, CN, NRR', and C$_{1-8}$alkylamino;

n is an integer between 1 and 4;

wherein a thioamide of formula 3:

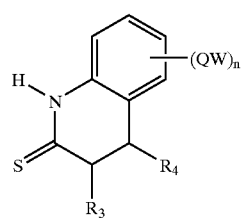

wherein R$_3$ and R$_4$ are as above defined, is N-alkylated with a vinyl ketone of formula 2:

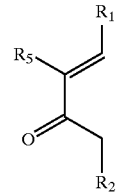

wherein R$_1$, R$_2$ and R$_3$ are as above defined to give the corresponding compound 4:

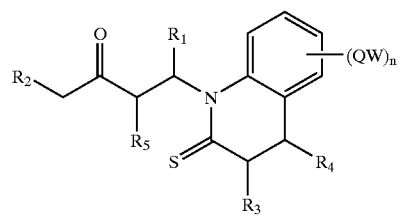

wherein all of the substituents are as above defined, said compound 4 being methylated, at the sulfur atom to give the salt of formula 5:

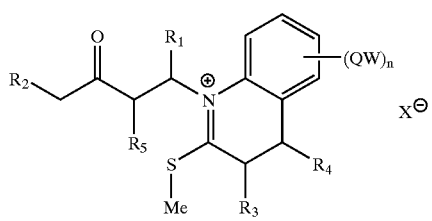

wherein all the substituents are as above defined, said compound of formula 5 being directly reacted with a base to give compound 1.

3. Process for the preparation of compound of formula (I):

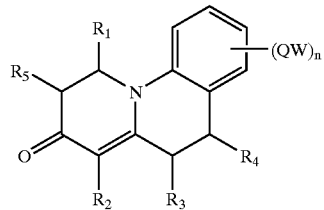

wherein:

R$_1$, R$_2$, R$_3$, R$_4$, R$_5$, are the same or different, and are selected from the group consisting of H, C$_{1-8}$ alkyl, C$_{2-8}$ alkenyl, C$_{2-8}$alkinyl, cyclopropane, cyclobutane, cyclopentane, cyclohexane, cycloheptane, and halogen;

Q is selected from the group consisting of a simple bond, C$_{1-8}$alkyl, C$_{2-8}$alkenyl, C$_{2-8}$alkinyl cyclopropane, cyclobutane, cyclopentane, cyclohexane and cycloheptane;

W is selected from the group consisting of H, C$_{1-8}$alkyl and C$_{2-8}$alkenyl; and n is 1–4;

wherein a thioamide of formula 3:

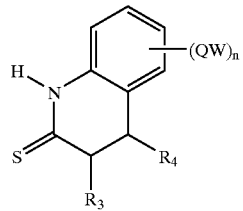

3 wherein $R_3$ and $R_4$ are as above defined, is N-alkylated with a vinyl ketone of formula 2:

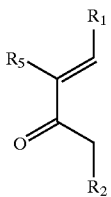

2 wherein $R_1$, $R_2$ and $R_3$ are as above defined to give the corresponding compound of formula 4:

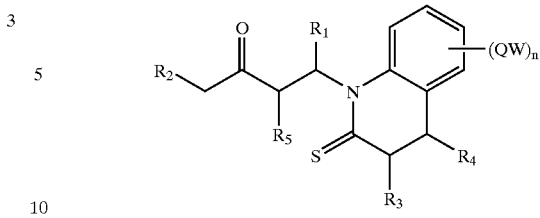

4 wherein all of the substituents are as above defined, compound 4 being methylated, at the sulfur atom to give the salt of formula 5:

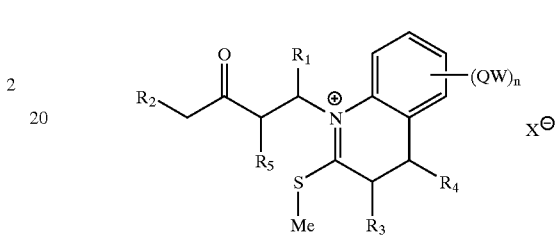

5 wherein all the substituents are as above defined, said compound of formula 5 being directly reacted with a base to give compound of formula 1.

* * * * *